United States Patent [19]
Yazawa et al.

[11] Patent Number: 4,981,805
[45] Date of Patent: Jan. 1, 1991

[54] METHOD OF USING CHEMICAL ANALYSIS SLIDE

[75] Inventors: Kenichiro Yazawa; Masao Kitajima; Asaji Kondo, all of Saitama, Japan

[73] Assignee: Fuji Photo Film Co., Ltd., Kanagawa, Japan

[21] Appl. No.: 682,478

[22] Filed: Dec. 17, 1984

Related U.S. Application Data

[63] Continuation of Ser. No. 225,819, Jan. 16, 1981, abandoned.

[30] Foreign Application Priority Data

Jan. 18, 1980 [JP] Japan ................................ 55-3606

[51] Int. Cl.$^5$ .............................................. G01N 21/78
[52] U.S. Cl. .................................... 436/169; 356/246; 422/56; 422/58; 422/102; 436/165
[58] Field of Search ................ 422/55, 56, 57, 58, 422/102; 128/760; 356/246; 350/92, 95; 436/169, 165

[56] References Cited

U.S. PATENT DOCUMENTS

| | | | |
|---|---|---|---|
| 2,292,450 | 8/1942 | Kohn | 128/760 X |
| 2,561,339 | 7/1951 | Chediak | 422/102 |
| 3,785,930 | 1/1974 | Ellis | 422/56 X |
| 3,814,668 | 6/1974 | Blake et al. | 435/805 X |
| 3,884,641 | 5/1975 | Kraffczyk et al. | 422/58 X |
| 3,990,850 | 11/1976 | Friedman et al. | 422/55 X |
| 4,176,174 | 11/1979 | Russell et al. | 422/55 X |
| 4,230,757 | 10/1980 | Toner | 422/56 X |
| 4,256,693 | 5/1981 | Kondo et al. | 422/56 |
| 4,298,571 | 11/1981 | Fulvio et al. | 422/65 |

FOREIGN PATENT DOCUMENTS

| | | | |
|---|---|---|---|
| 162293 | 11/1979 | Japan . | |
| 0162294 | 11/1979 | Japan | 422/58 |
| 10620 | 4/1984 | Japan . | |

Primary Examiner—Robert J. Hill, Jr.
Attorney, Agent, or Firm—Sughrue, Mion, Zinn, Macpeak & Seas

[57] ABSTRACT

A method of using a chemical analysis slide comprising a slide frame and a sheet-like or film-like chemical analysis element for colorimetric determination of a specific component in an aqueous liquid sample, which comprises applying an aqueous liquid sample to the chemical analysis element, and covering the upper face of the side of the slide frame to which the sample is applied with a sheet-like, plate-like or block or brick-like cover to thereby ensure a space between the chemical analysis element and the cover and to prevent evaporation of water or to control evaporation rate of water.

9 Claims, 1 Drawing Sheet

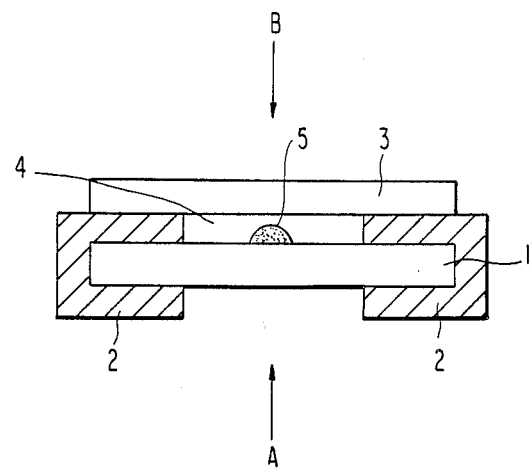

METHOD OF USING CHEMICAL ANALYSIS SLIDE

This is a continuation of application Ser. No. 225,819, filed Jan. 16, 1981 now abandoned.

FIELD OF THE INVENTION

This invention relates to a method of using a chemical analysis slide for colorimetric determination of a specific chemical component in an aqueous liquid sample.

BACKGROUND OF THE INVENTION

Many sheet-like or film-like analysis elements for colorimetric determination of a specific component in an aqueous liquid sample have been reported so far. For example, "stick type" or "chip type" materials comprising a filter-paper matrix having impregnated therein an analytical reagent or reagents are described in Japanese Patent Publication No. 14673/69, etc. Multi-layered type integral chemical analysis elements (sheets or films) for quantitative analysis of a certain component in body fluids such as blood or urine are described in Japanese patent applications (OPI) Nos. 53888/74 (U.S. Pat. Nos. 3,992,158), 137192/75 (U.S. Pat. No. 3,983,005), 40191/76 (U.S. Pat. No. 4,042,335), 3488/77 (U.S. Reissue Pat. No. 30,267), 131786/77 (U.S. Pat. No. 4,050,898) and 142584/77 (U.S. Pat. No. 4,053,381, 4,171,246 and 4,214,968), U.S. Pat. Nos. 3,992,158, 3,526,480, etc. (The term "OPI" as used herein refers to a "published unexamined Japanese patent application".) The latter analysis sheets have a structure comprising a transparent support with one or two reagent layers superposed thereon and, further, a porous spreading layer integrally thereon so that such is not separated from each other, or have a structure composed of the above-described two layers alone. These sheet-like chemical analysis elements are often used in a form retained in a slide frame as shown in *CHEMICAL WEEK*, No. 1978-Aug.-23, p. 55 or U.S. Pat. No. 4,142,863. Analysis elements comprising a combination of a slide frame and a sheet-like or film-like chemical analysis element will be hereinafter referred to as "chemical analysis slides" in this specification.

In quantitative analysis using such analysis elements, a specific component in an aqueous liquid sample reacts with a reagent contained in the analysis element, and the degree of coloration or discoloration is measured using transmitted or reflected light. Many of the reactions utilize a coloration reaction with an organic reagent in water, and hence even reactions proceeding with a faster rate require one minute or more and reactions proceeding with a slower rate, for example, those using an enzyme, often require 5 to 10 minutes under incubation at 35° C. to 37° C. In these reactions, the presence of a sufficient amount of water is necessary until completion of the reaction. The thickness of a reagent layer of an ordinarily used sheet-like or film-like chemical analysis element is as thin as several tens of micrometers, and therefore the water-retaining ability of the reagent layer is not sufficient. Thus, evaporation of water proceeds from the surface of the chemical analysis element to an extent that accurate quantitative analysis becomes difficult due to the change in water content in the reaction system of the reagent layer during the course of incubation or, in the case where the reduction in water content is serious, the reaction stops. In addition to the evaporation of water, migration of reaction products produced in the reaction system into other layers than the reaction layer or the detection layer, such as a light-blocking layer, a spreading layer, and the like caused by migration of water results in a failure to attain accurate quantitative analysis.

For the purpose of removing these defects, Japanese Utility Model Application (OPI) Nos. 162293/79 and 162294/79 describe the presence of a water evaporation-preventing cover on a multilayered chemical analysis element. It has been confirmed that the means described therein prevents evaporation of water from the sample-applied portion and accelerates completion of the reaction between a specific component in the sample and a reagent in the analysis element, thus serving to improve analysis accuracy.

However, based on the descriptions in these patent specifications, the applied sample comes into direct contact with the water evaporation-preventing cover, and this contact might result in staining of the sample and, in the case where the reaction between a specific component in the sample and a reagent in the analysis element requires air (or oxygen), the contact in some cases provides unfavorable results. For example, in detecting glucose, cholesterol, uric acid, neutral fats, or the like utilizing an oxidase-containing reagent, supply of air into the reaction system is necessary because the step of producing $H_2O_2$ by the action of oxidase greatly depends upon the amount of oxygen which is also present. Therefore, the approach set forth in the above-described two utility model applications is not suitable for such a reaction system.

SUMMARY OF THE INVENTION

As a result of intensive investigations as to a method of using a known chemical analysis slide composed of a slide frame and a sheet-like or film-like chemical analysis element for colorimetric determination of a specific component in an aqueous sample, it has now been unexpectedly found that analysis accuracy can be remarkably increased by covering, after application of an aqueous liquid sample to the sheet-like or film-like chemical analysis element, the upper face of the side of the slide frame to which the sample is applied, thus having achieved the present invention.

That is, the present invention provides a method of using a chemical analysis slide composed of a slide frame and a sheet-like or film-like chemical analysis element for colorimetric determination of a specific component in an aqueous liquid sample, which comprises applying an aqueous liquid sample to the sheet-like or film-like chemical analysis element, and covering the upper face of the side of the slide frame to which the sample is applied with a sheet-like, plate-like or block or brick-like cover to thereby ensure a space between the sheet-like or film-like chemical analysis element and the cover and to prevent evaporation of water or to control evaporation rate and humidity.

BRIEF DESCRIPTION OF THE DRAWING

The Figure is a schematic view illustrating the method of the present invention, wherein numeral 1 designates a sheet-like or film-like chemical analysis element, 2 a slide frame, 3 a cover, 4 a space, 5 an aqueous liquid sample, and A and B each the measurement direction.

DETAILED DESCRIPTION OF THE INVENTION

According to the method of the present invention, evaporation of water present in a sample can be prevented or the evaporation rate can be controlled by providing a cover on a chemical analysis slide and, where the reaction between a sample and a reagent contained in a chemical analysis element yields a volatile reaction product such as ammonia or carbon dioxide, loss thereof is also controlled. Further, the amount of air or oxygen supplied is controlled as well. Still further, staining upon handling of the chemical analysis slide can be prevented and the use of a cover which can be written upon facilitating sample designation and recording of data.

In the method of the present invention, covers with various shapes such as a sheet-like cover, a plate-like cover, and a block or brick-like cover can be used as the cover for covering the slide frame. Appropriate covers may be selected and used depending upon the kind of reaction system and end-use. Suitable sheet-like materials include paper, synthetic resin films, cloth, etc. For example, where the reaction requires a large amount of oxygen, may be used a porous material such as paper or cloth previously rendered air-permeable and water-impermeable by treatment with a fluorocarbon resin or a silicone resin. Exemplary plate-like materials are synthetic resin plates or metal plates. Further, where mechanical automatic analysis is desired, the upper face of a slide frame can be effectively covered by a plate-like or block or brick-like material provided in the analytical apparatus after application of a sample and the material removed after completion of the analysis.

The cover is desirably placed immediately after application of a sample and must be kept in place at least until optical measurement.

The cover may be provided as an "open-close" type cover partly adhered to part of the slide frame, or may be merely placed or bonded onto the upper face of the slide frame after application of a sample.

The method of the present invention enables a uniform color with good reproducibility to be obtained and the rate of reaction between a specific component in the sample and a reagent in the analysis element to be increased, i.e., to make uniform and accelerate diffusion of reactants through the layer.

The method of the present invention is particularly effective for analysis of an aqueous liquid sample, in particular, body fluids (e.g., blood, urine, saliva, spinal fluid, etc.).

Colorimetric determination is conducted by measuring the optical density. In the case of measuring with the cover on, reflected light is measured from the opposite side to the side on which the cover is placed and, in the case of measuring with the cover off, either reflected light or transmitted light may be measured for the determination.

The method of the present invention will be described by reference to a schematic view shown in the FIGURE. A chemical analysis slide is formed by a slide frame 2 and a sheet-like or film-like chemical anaylsis element 1. After application of an aqueous liquid sample 5 to the sheet-like or film-like chemical analysis element 1, the slide frame 2 is covered by a cover 3 to ensure space 4 between the chemical analysis element 1 and the cover 3. A specific component in the sample 5 reacts with a reagent contained in the chemical analysis element to cause coloration or discoloration, the degree of which is determined in the direction of A or B by measuring the transmitted or reflected light.

The present invention is described in more detail by reference to following Examples which, however, are not to be construed as limiting the present invention in any way.

EXAMPLE 1

(A) Preparation of Film-Like Chemical Analysis Element:

On a subbed, 185-$\mu$m thick transparent polyethylene terephthalate (PET) film was coated a solution composed of 50 mg of glucose peroxidase (GOD III, made by Toyo Spinning Co., Ltd.), 20 mg of peroxidase (POD III,. made by Toyo Spinning Co., Ltd.), 135 mg of 1,7-dihydroxynaphthalene, 180 mg of 4-aminoantipyrine, 20 mg of polyoxyethylene nonylphenyl ether (Nonion HS 210, made by Nippon Oils & Fats Co., Ltd.), 8.5 g of gelatin, and 100 ml of water in a dry thickness of 15 $\mu$m.

Then, a uniform dispersion composed of 6.8 g of titanium oxide, 2.7 g of gelatin, 100 mg of polyoxyethylene nonylphenyl ether, and 50 g of water was coated thereon in a dry thickness of 8 $\mu$m.

Furthermore, a cotton broad cloth (made by using two folded yarns of a yarn number count of 100, manufactured by Toyo Spinning Co., Ltd.) treated with a 0.2% polyoxyethylene nonylphenyl ether was press-laminated thereon to provide a porous spreading layer, and thus a film-like chemical analysis element was prepared.

(B) Preparation of Chemical Analysis Slide:

Slide frames were produced by assembling 24$\times$28 mm plates with an aperature of 10 mm in diameter at the center as lower and upper plates and a 24$\times$28 mm plate with 16$\times$16 mm square aperture at the center as an intermediate plate, using 0.5 mm thick polyvinyl chloride planar plates. Then, a 16$\times$16 mm film-like chemical analysis element prepared in (A) was inserted therein to prepare a chemical analysis slide having the structure shown in the FIGURE (with cover 3 off).

(C) Determination of Glucose Level:

10 $\mu$l portions of blood serum samples with different glucose levels were applied to the porous spreading layer of the chemical analysis element of the chemical analysis slide prepared in (B) and, after incubation at 35° C. for 10 minutes, the reflection optical density (OD) was measured at a wavelength of 500 nm.

Using the same procedures, a 20$\times$24 mm sheet-like cover prepared by coating an acrylic adhesive on one side of a 100 $\mu$m thick paper was applied immediately after application of the blood serum sample so as to close the circular aperture of the upper face of the slide frame.

Thus, the results as shown in Table 1 below were obtained.

TABLE 1

| | Blood Serum Sample No. | | | | |
|---|---|---|---|---|---|
| | 1 | 2 | 3 | 4 | 5 |
| Glucose Level in Sample | 100 | 200 | 300 | 400 | 500 |
| $OD_{500}$ | | | | | |
| With cover on | 0.57 | 0.86 | 1.14 | 1.38 | 1.49 |
| With cover off | 0.50 | 0.80 | 0.96 | 1.17 | 1.26 |

As is shown in Table 1, the color optical density was clearly increased by application of the cover sheet. This effect is particularly marked with blood serum samples containing glucose at a high level which requires a large amount of time for completion of the reaction.

EXAMPLE 2

The same procedures as in Example 1, (C), were conducted except for using a 1 mm thick, 20×24 mm polyvinyl chloride planar plate in place of the adhesive cover sheet. Immediately after application of the blood serum sample, the above-described planar plate was applied so as to close the aperture of the slide frame, and allowed to stand during incubation at 35° C. for 10 minutes. After the incubation time elapsed, the above-described planar plate was removed, and the reflection optical density was measured from the transparent support side opposite to the side to which the sample had been applied using light of a wavelength of 500 nm. For the purpose of comparison, incubation was conducted without using the planar plate, followed by measurement of the reflection optical density.

The color optical density obtained in the case of applying the planar plate to control evaporation of water was about 10 to about 20% greater than that in the case of where the planar plate was not applied.

EXAMPLE 3

The same procedures as in Example 1, (C), were conducted except for changing the space volume between the film-like chemical analysis element and the cover sheet to determine the influences of the change on the color optical density. For comparison, the direct application of the cover sheet onto the upper face of the porous spreading layer of the chemical analysis element was also evaluated. As the sample, heparinized fresh blood was used in place of blood serum. The results thus obtained are tabulated in Table 2 below.

TABLE 2

|  | Space Volume (relative value) | Blood Glucose Level (mg/dl) | | |
|---|---|---|---|---|
|  |  | 93 | 218 | 283 |
| Reflection O.D. (500 nm) | 0 | 0.42 | 0.50 | 0.73 |
|  | 100 | 0.57 | 0.77 | 0.94 |
|  | 200 | 0.62 | 0.86 | 0.99 |
|  | 300 | 0.71 | 0.95 | 1.06 |

The results in Table 2 clearly shows the following: Where the space volume is zero (that is, where the cover sheet is directly applied to the upper face of the porous spreading layer of the film-like chemical analysis element), unstable coloration possibly due to insufficient supply of oxygen results and the correlation coefficient between blood glucose level and the reflection optical density is small. On the other hand, where a definite space volume is ensured, the correlation coefficient between blood glucose level and reflection optical density is approximately 1 (an about linear relationship), and the reflection optical density itself increases by about 30% to about 100%.

While the invention has been described in detail and with reference to specific embodiments thereof, it will be apparent to one skilled in the art that various changes and modifications can be made therein without departing from the spirit and scope thereof.

What is claimed is:

1. In a method for the colorimetric determination of a specific component in an aqueous liquid sample by applying the aqueous liquid sample to a chemical analysis element for the colorimetric determination, wherein the chemical analysis element is covered after the sample is applied to prevent the evaporation of water, the improvement comprising:

applying a blood sample, as the aqueous liquid sample, to said chemical analysis element, said chemical analysis element being a component of a chemical analysis slide comprised of a slide frame and a sheet-like or film-like chemical analysis element for the colorimetric determination, and covering the upper face of the side of said slide frame which contains the chemical analysis element to which said blood sample is applied with a sheet-like, plate-like or block or brick-like cover to thereby ensure a space between said chemical analysis element and said cover and to either present evaporation of water, or to control the evaporation rate of water, and to control the amount of air or oxygen reaching said aqueous liquid blood sample.

2. The method of claim 1, wherein said cover is a sheet-like material of paper, a synthetic resin film or cloth.

3. The method of claim 2, wherein said evaporation rate of water is controlled.

4. The method of claim 1, wherein said cover is a porous material which is both air-permeable and water-impermeable.

5. The method of claim 1, wherein said cover is partly adhered to the slide frame permitting the cover to be opened and then closed.

6. The method of claim 1, wherein said cover is a plate-like material of a synthetic resin.

7. The method of claim 1, wherein said cover is a metal plate.

8. The method of claim 1, wherein said covering is conducted by placing the cover onto the upper face of the slide frame.

9. The method of claim 1, wherein said covering is conducted by bonding the cover onto the upper face of the slide frame.

* * * * *

UNITED STATES PATENT AND TRADEMARK OFFICE
CERTIFICATE OF CORRECTION

PATENT NO. : 4,981,805

DATED : January 1, 1991

INVENTOR(S) : Yazawa, et al

It is certified that error appears in the above-identified patent and that said Letters Patent is hereby corrected as shown below:

Column 6, line 30, in claim 1, delete "present" and insert --prevent--.

Signed and Sealed this

Twenty-second Day of September, 1992

Attest:

DOUGLAS B. COMER

*Attesting Officer*  *Acting Commissioner of Patents and Trademarks*